United States Patent [19]

Fleming

[11] Patent Number: Plant 7,444

[45] Date of Patent: Feb. 12, 1991

[54] KALANCHOE PLANT NAMED BIG SURPRISE

[75] Inventor: Margaret M. Fleming, Soquel, Calif.

[73] Assignee: The Plant Company, Soquel, Calif.

[21] Appl. No.: 385,162

[22] Filed: Jul. 26, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Big Surprise particularly characterized by its coral-red flower color with red highlights; flower diameter of 16 to 17 mm at maturity; flowering response, from 9 weeks in summer to 11 weeks in winter after start of short days; excellent keeping quality of flowers and foliage; branches freely with or without pinching; vigorous plant with short internodes; responsive to B-9 to reduce internode length and peduncle elongation; and adaptability to various pot sizes.

2 Drawing Sheets

The present invention relates to a new and distinctive cultivar of kalanchoe plant, botanically known as *Kalanchoe blossfeldiana* Poelln., and referred to by the cultivar name Big Surprise.

Big Surprise, identified as 406-260, is a product of a planned breeding program which had the objective of creating new kalanchoe cultivars for year-round commercial production having an earlier flowering response, well branched yet compact flowering plants, suitability for flowering in pots ranging from 10 to 15 cm, and with good flower and foliage keeping quality.

Big Surprise was originated from a cross made by the inventor Margaret M. Fleming in a controlled breeding program in Half Moon Bay, Calif., in 1983.

The female parent of Big Surprise was the cultivar identified as Eternity, disclosed in U.S. Plant Pat. No. 5,253. The male parent was the cultivar identified as Cinnabar, disclosed in U.S. Plant Pat. No. 5,160.

Big Surprise was discovered and selected as one flowering plant within the progeny of the stated cross by Margaret M. Fleming in September of 1984 in a controlled environment in Half Moon Bay, Calif.

The first act of asexual reproduction of Big Surprise was accomplished when vegetative cuttings were taken from the initial selection in January of 1985 in a controlled environment in Half Moon Bay, Calif., by Margaret M. Fleming.

Horticultural examination of controlled flowerings of successive plantings has shown that the unique combination of characteristics as herein disclosed for Big Surprise are firmly fixed and are retained through successive generations of asexual reproduction. Big Surprise has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Big Surprise, which, in combination, distinguish this kalanchoe as a new and distinct cultivar:

1. Coral-red flower color with red highlights.

2. Flower diameter of 16–17 mm at maturity.
3. Flowering response of from 9 weeks in summer to 11 weeks in winter, from start of short day treatments.
4. Excellent keeping quality of both flowers and foliage.
5. Branches freely with or without pinching.
6. Vigorous plant with short internodes.
7. Good responsiveness to B-9 to reduce internode length and peduncle elongation.
8. Proper scheduling makes this new cultivar suitable for production in 10 cm to 15 cm pots.

The accompanying colored photographic drawings show typical inflorescence and leaf characteristics of Big Surprise, with colors being as nearly true as possible with illustrations of this type.

Sheet 1 is a color photograph showing in perspective view a plant of Big Surprise grown as a non-pinched flowering kalanchoe in a 10 cm pot.

Sheet 2 is a black and white photograph showing the leaves of Big Surprise at three stages of development (mature, intermediate and immature).

No commercial cultivar known to the inventor has the same flower color as Big Surprise. However, the female parent Eternity may be compared in several aspects. Similar traits are flower size, keeping quality of flowers and foliage, responsiveness to B-9, and adaptability to various pot sizes. In comparison to Eternity, Big Surprise has a much faster flowering response, has a darker flower color, branches more freely, has more vigorous growth, and has smaller, more lanceolate foliage.

In comparison to the male parent cultivar Cinnabar, both Big Surprise and Cinnabar are early blooming. However, Big Surprise flowers substantially longer. In addition, Big Surprise has larger flowers and a taller habit. The flower color of Cinnabar is red-orange and uniform, whereas Big Surprise is red-coral with deeper red highlights. Further, the foliage of Big Surprise is more lanceolate in shape, more serrated, more durable, darker green in color, and does not degrade with age when compared with the foliage of Cinnabar.

In comparison with the sister seedling Radiance, both are early blooming (9–11 weeks), and flower for long periods of time. Although the foliage of Big Surprise and Radiance is smaller than either parent, and is as durable as Eternity, the foliage of Big Surprise and Radiance are not alike in either color, form or size. Big Surprise is more vigorous and open than Radiance, and substantially taller. Although the flower colors of Big Surprise and Radiance are both coral and red, the coral tone in the flowers of Big Surprise is much more pronounced and the respective flower colors as a result are distinctly different.

In the following description color references are made to The Royal Horticultural Society Colour Chart. The color values were determined on plant material grown as a non-pinched pot plant in a 10 cm pot in Soquel, Calif., on Oct. 9, 1988.

Classification:

*Botanical.*—*Kalanchoe blossfeldiana* Poelln. cv. Big Surprise.

*Commercial.*—Flowering pot Kalanchoe.

Parentage:

*Female parent.*—Eternity.

*Male parent.*—Cinnabar.

Propagation:

(A) *Type cutting.*—Short tip cutting, with stems up to 2 cm.

(B) *Time to root.*—10 days at 21° C. in summer, 14 days at 21° in winter.

(C) *Rooting habit.*—Many very fine roots, fibrous.

Plant description:

(A) *Form.*—Vigorous, upright growth. Growing and scheduling practices can produce a small plant in a 10 cm pot up to a larger plant in a 15 cm pot.

(B) *Habit of growth.*—Rate of growth fast for this type of plant, with 3–4 applications of 3500 ppm B-9 SP growth regulation being the preferred regimen. Generally, shoots are formed at every node. Height of plant above 10 cm. pot is 20–30 cm; internode length of vegetative natural plant is 15–30 mm.

(C) *Foliage description.*—Leaves simple, opposite, slightly lobed. 1. Size: Average full grown leaf in a 10 cm flowering pot is 130 mm long×65 mm wide. 2. Shape: Ovate to elliptic, apex obtuse to slightly pointed, base attenuate. 3. Texture: Glabrous, coriaceous, succulent. 4. Margin: Sinuate to crenate. 5. Color: Mature foliage: Upper surface 147A; Under surface 147B. 6. Durability: Excellent. No degradation observed, even the lower foliage of plants retained for months beyond normal expectancy.

Flowering description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (each of which is 12–17 mm. in length) will continue for two months or more. Individual flowers last two weeks or more after opening.

(B) *Flowering response.*—Flowering time under controlled daylength after start of short days is 9 weeks in summer to 11 weeks in winter.

(C) *Flowers borne.*—Compound dichasial cymes; peduncle length 5–15 cm., diameter 3–7 mm.; pedicel length 5–7 mm., diameter approximately 1.0 mm.

(D) *Quantity of flowers.*—Highly floriferous, with up to 100 flowers per major inflorescence and up to 500 flowers per plant in a 10 cm. pot produced in accordance with commercial culture; high number of flowers on both main axis and side laterals, with 4 to 6 side laterals in a 10 cm pot.

(E) *Petals.*—1. Shape: Slightly pointed to almost round. Petals slightly bend down when flowers are fully open. 2. Color: Upper surface: 41B, highlighted with 41A. Under surface: 37C, slightly streaked with 41B. 3. Number of petals: 4, united in corolla. 4. Flower diameter: 16 to 17 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, size 4 mm long, color light green.

(G) *Keeping qualities.*—Excellent. Each floret can be expected to last two weeks or more, and the plant itself many weeks.

Disease resistance: Resistant to Botrytis and Powdery Mildew. To date chlorosis, necrotic spots, stem rot, root rot and tip die-back have not been observed.

Fragrance: No perceptible fragrance of flowers or foliage.

I claim:

1. A new and distinct plant of Kalanchoe named Big Surprise, as described and illustrated.

* * * * *

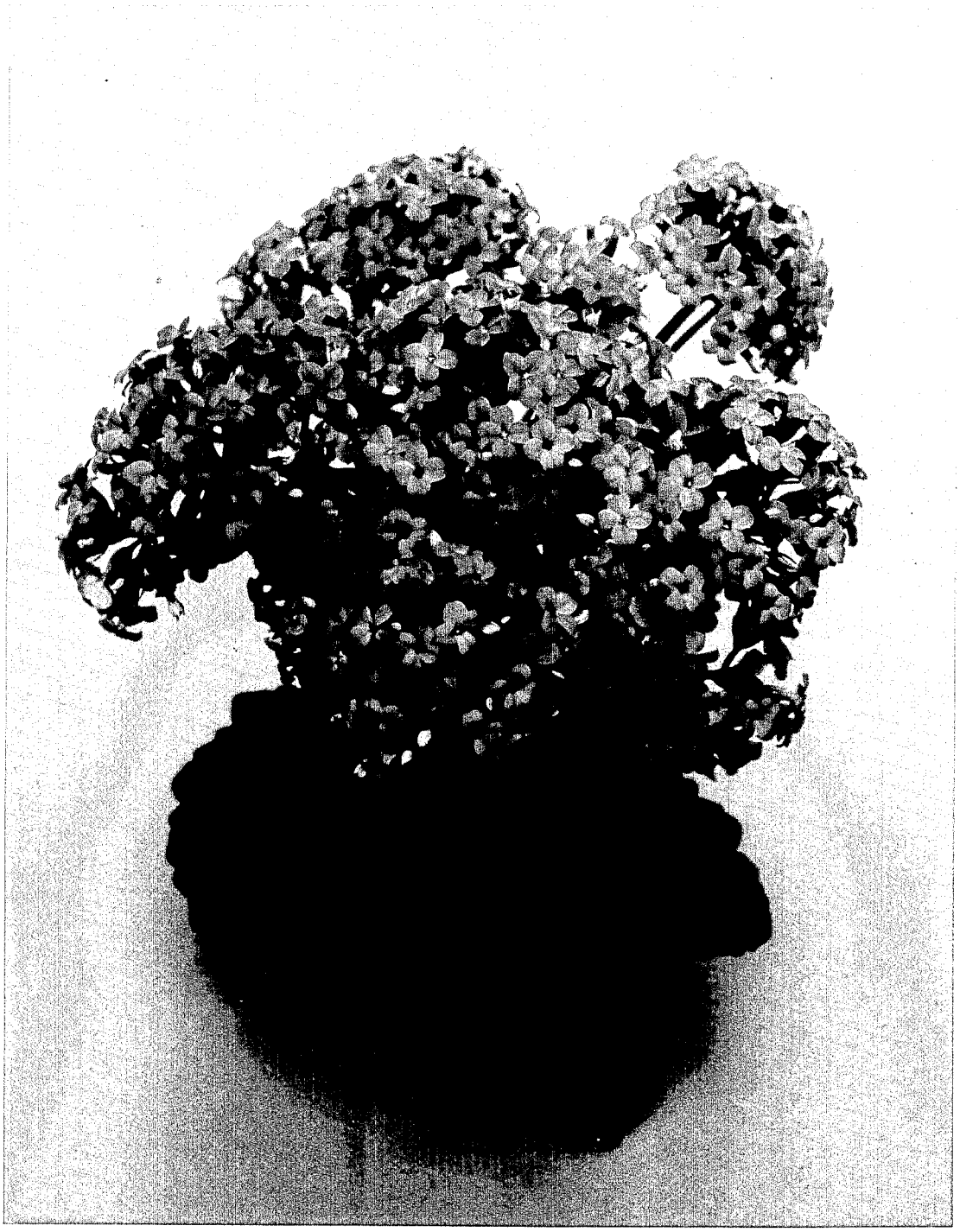

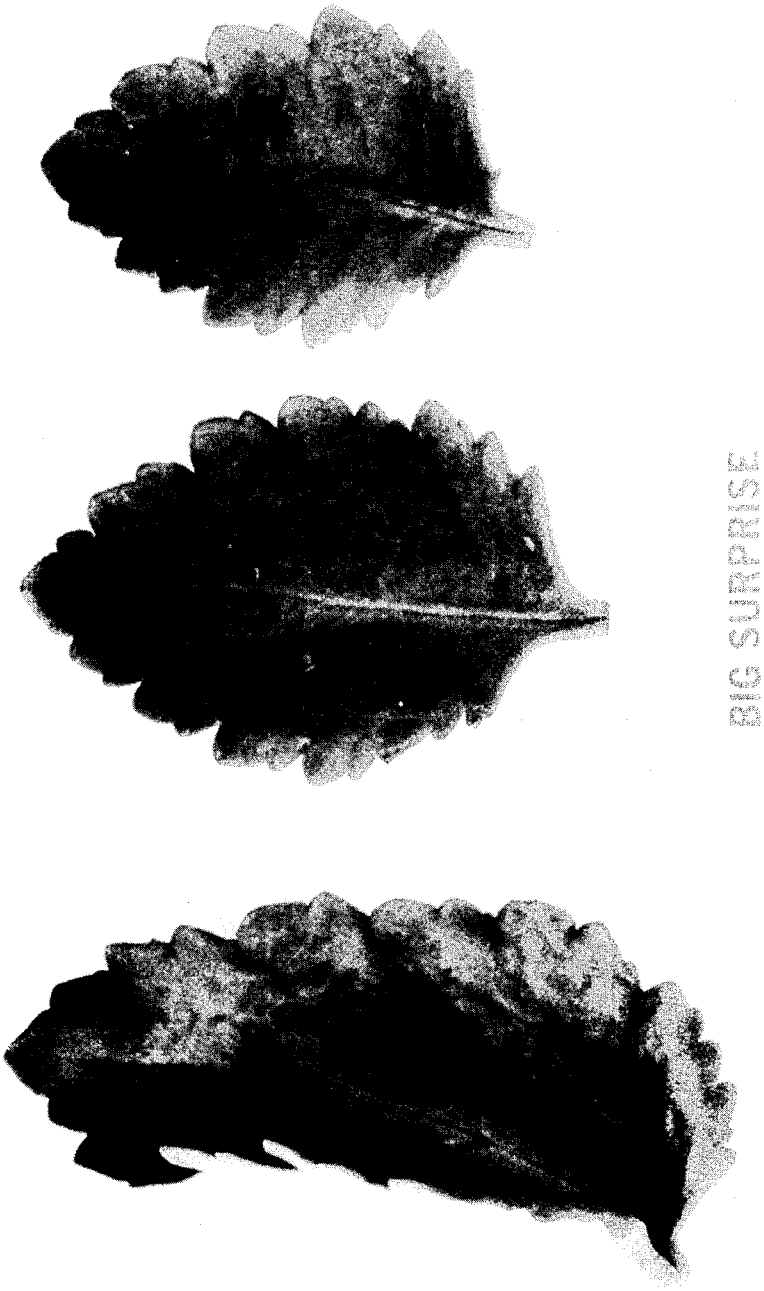
BIG SURPRISE